United States Patent
Von Schuckmann

(10) Patent No.: US 9,095,667 B2
(45) Date of Patent: Aug. 4, 2015

(54) SYRINGE CAP

(75) Inventor: Alfred Von Schuckmann, Kevelaer (DE)

(73) Assignee: SCHOTT Schweiz AG, St. Gallen (CH)

( * ) Notice: Subject to any disclaimer, the term of this patent is extended or adjusted under 35 U.S.C. 154(b) by 0 days.

(21) Appl. No.: 13/988,528

(22) PCT Filed: Dec. 1, 2011

(86) PCT No.: PCT/EP2011/071471
§ 371 (c)(1),
(2), (4) Date: May 21, 2013

(87) PCT Pub. No.: WO2012/076388
PCT Pub. Date: Jun. 14, 2012

(65) Prior Publication Data
US 2013/0237911 A1 Sep. 12, 2013

(30) Foreign Application Priority Data
Dec. 7, 2010 (DE) .......................... 10 2010 061 061

(51) Int. Cl.
*A61M 5/50* (2006.01)
*A61M 39/04* (2006.01)
*A61M 5/31* (2006.01)

(52) U.S. Cl.
CPC ........... *A61M 5/5086* (2013.01); *A61M 39/045* (2013.01); *A61M 2005/312* (2013.01); *A61M 2005/3104* (2013.01)

(58) Field of Classification Search
CPC ................. A61M 5/5086; A61M 5/50; B65D 2101/0046

USPC ................................................... 604/110, 111
See application file for complete search history.

(56) References Cited

U.S. PATENT DOCUMENTS

| 5,114,029 A * | 5/1992 | Gibilisco ....................... 215/220 |
| 6,193,688 B1 * | 2/2001 | Balestracci et al. .......... 604/111 |
| 6,196,998 B1 | 3/2001 | Jansen et al. |
| 6,264,052 B1 * | 7/2001 | Schmitz ........................ 215/252 |
| 6,520,935 B1 | 2/2003 | Jansen et al. |
| 6,585,691 B1 * | 7/2003 | Vitello .......................... 604/111 |
| 6,942,643 B2 * | 9/2005 | Eakins et al. ................. 604/111 |
| 7,367,964 B2 * | 5/2008 | Heinz et al. ................... 604/263 |

(Continued)

FOREIGN PATENT DOCUMENTS

| DE | 199 56 243 | 5/2000 |
| FR | 782 818 | 6/1935 |
| WO | WO 2009/028946 | 3/2009 |

OTHER PUBLICATIONS

International Search Report of PCT/EP2011/071471, date of mailing Apr. 19, 2012.

*Primary Examiner* — Gerald Landry, II
(74) *Attorney, Agent, or Firm* — Collard & Roe, P.C.

(57) ABSTRACT

The invention relates to a syringe cap (1) for a medical syringe (28), having two cap parts (2, 3) displaceable toward each other, wherein a motion of the cap parts (2, 3) toward each other takes place when the syringe cap (1) is first removed from the syringe (28). In order to disclose a syringe cap for a medical syringe, wherein a first use can be advantageously determined and handling is simple, according to the invention an indicator element is displaced into a display setting and the display element (6) can be removed from the syringe (28) together with the cap parts (2, 3) of the syringe cap (1).

18 Claims, 18 Drawing Sheets

(56) References Cited

U.S. PATENT DOCUMENTS

| | | | |
|---|---|---|---|
| 2001/0003150 A1* | 6/2001 | Imbert | 604/256 |
| 2004/0225258 A1* | 11/2004 | Balestracci | 604/111 |
| 2008/0097386 A1* | 4/2008 | Osypka | 604/510 |
| 2008/0171981 A1* | 7/2008 | Khan et al. | 604/111 |
| 2010/0185148 A1* | 7/2010 | Gillespie et al. | 604/110 |
| 2011/0062106 A1 | 3/2011 | Akveld | |
| 2011/0303670 A1* | 12/2011 | Baker | 220/257.1 |
| 2012/0109059 A1* | 5/2012 | Ranalletta et al. | 604/111 |

\* cited by examiner

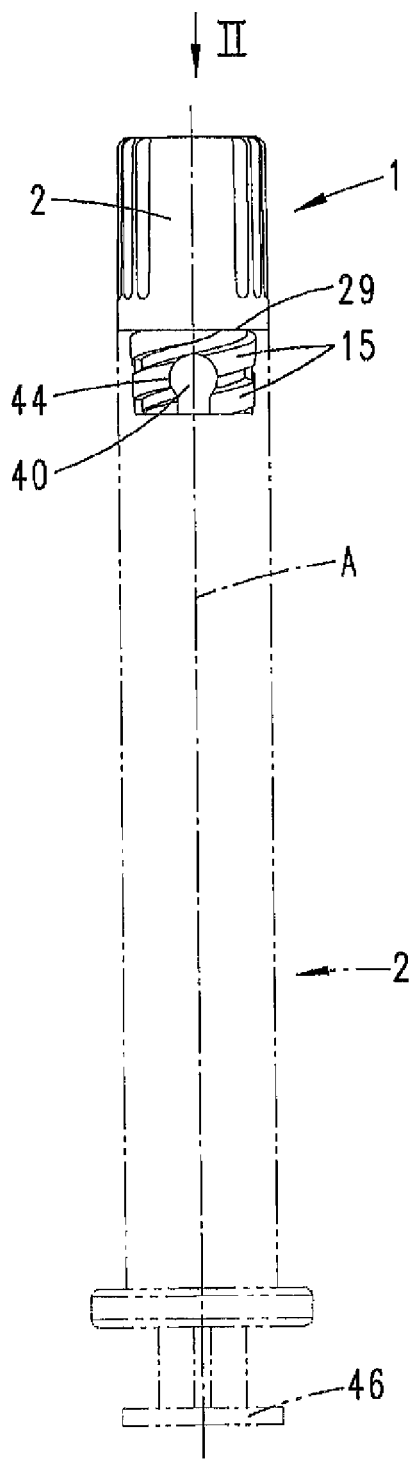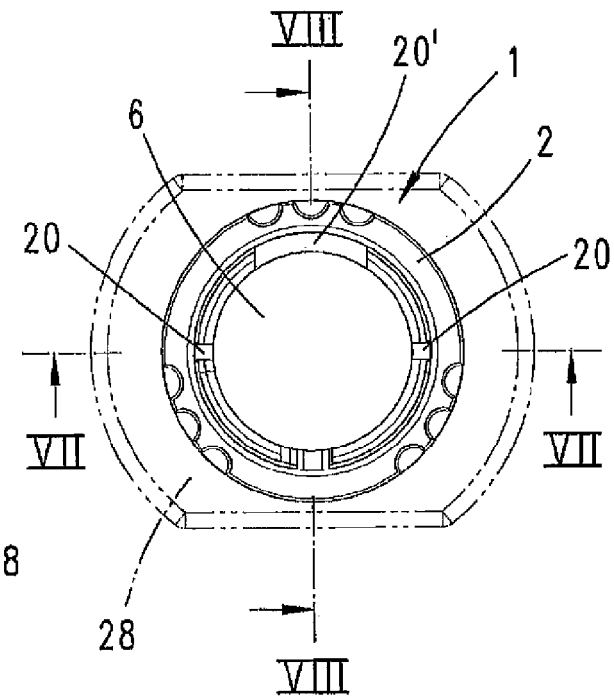

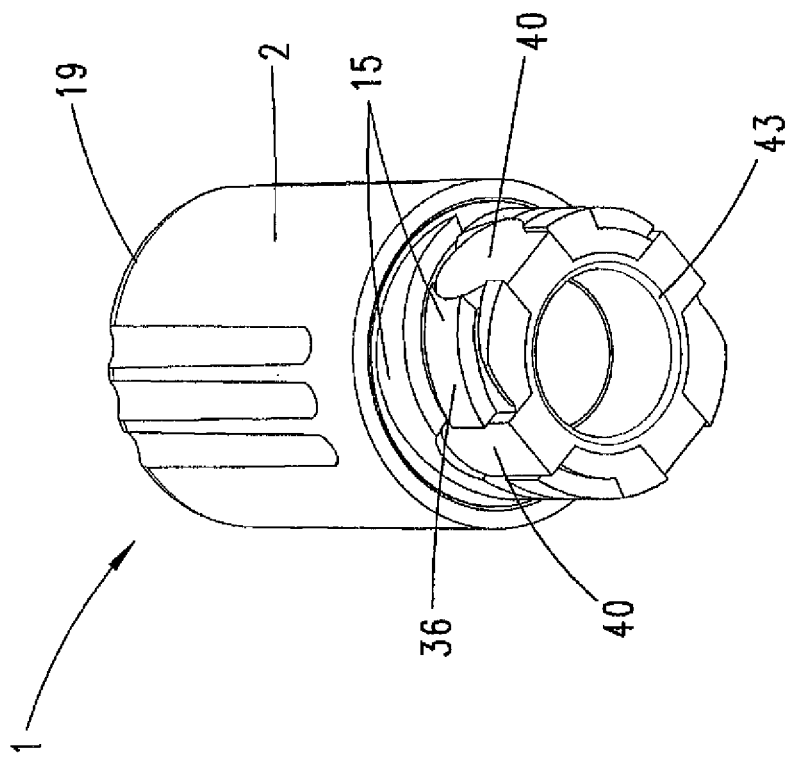
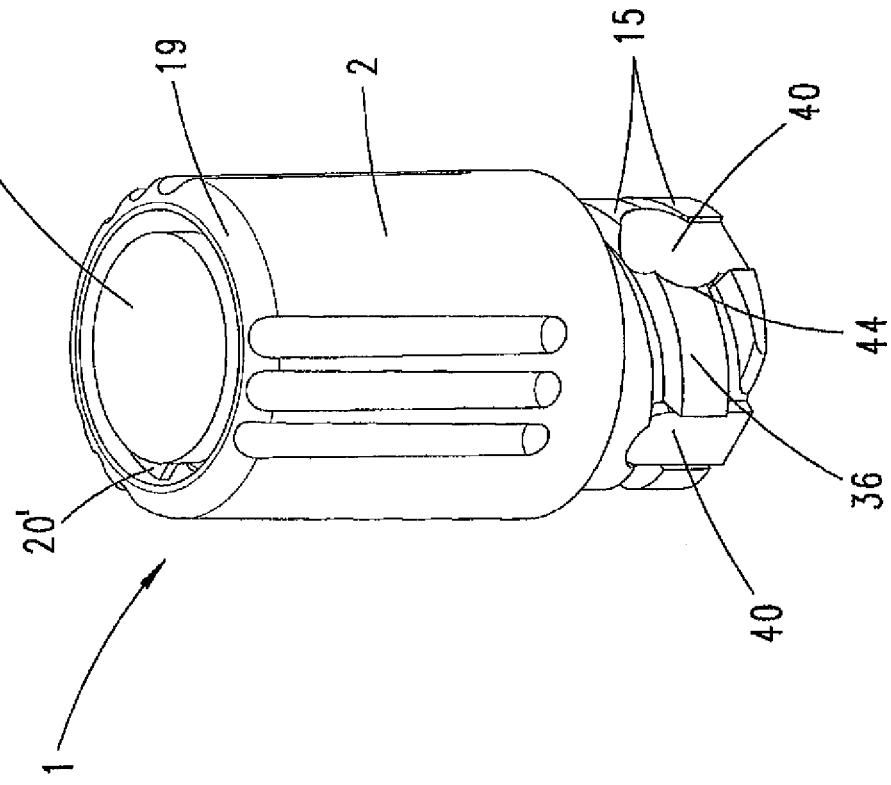

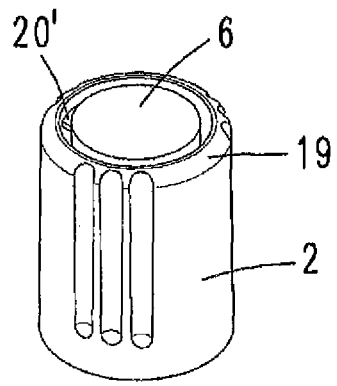
Fig. 5
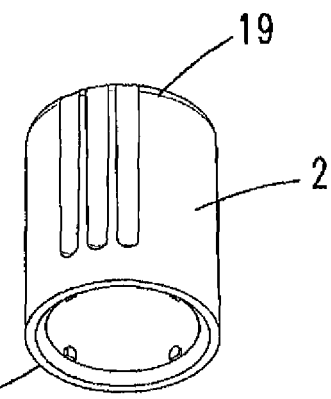
Fig. 6
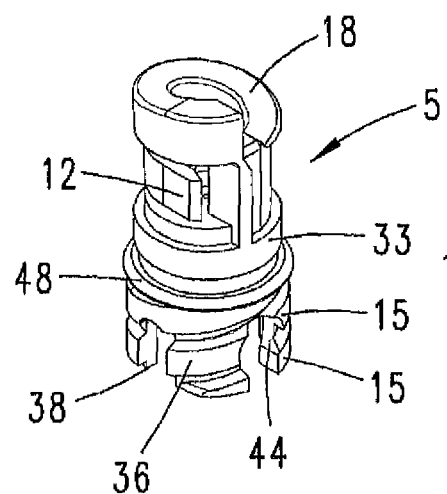
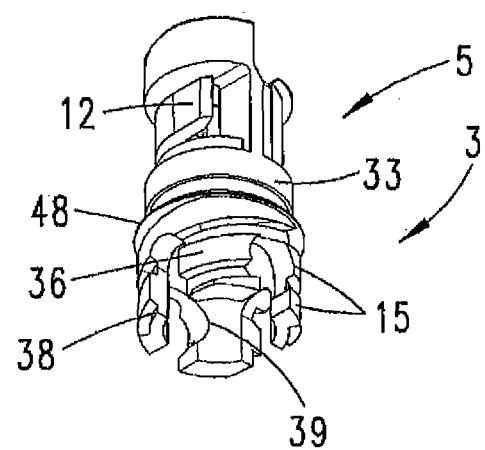
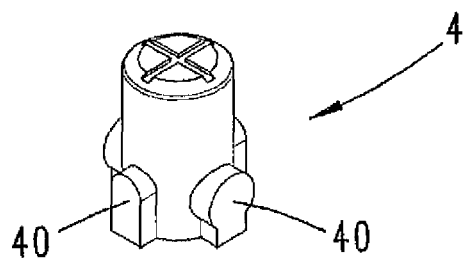
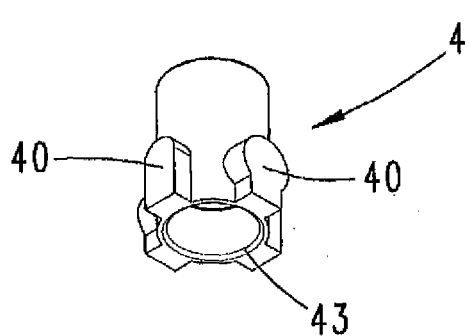
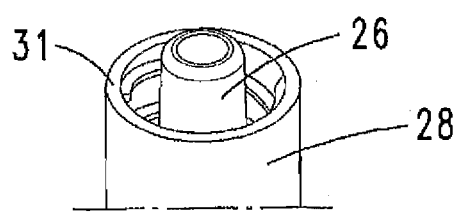
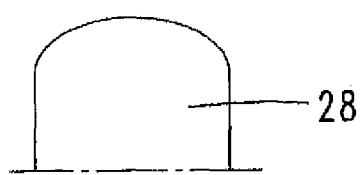

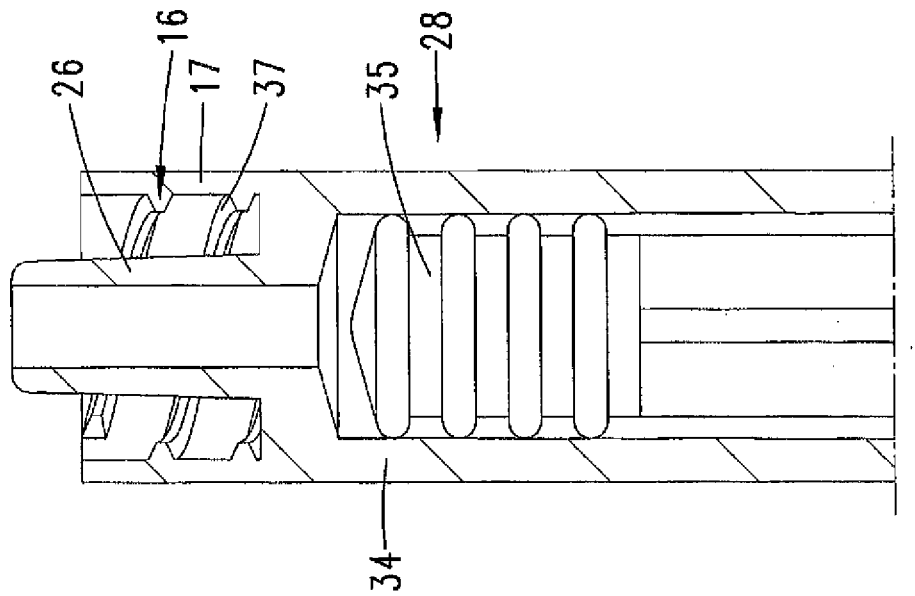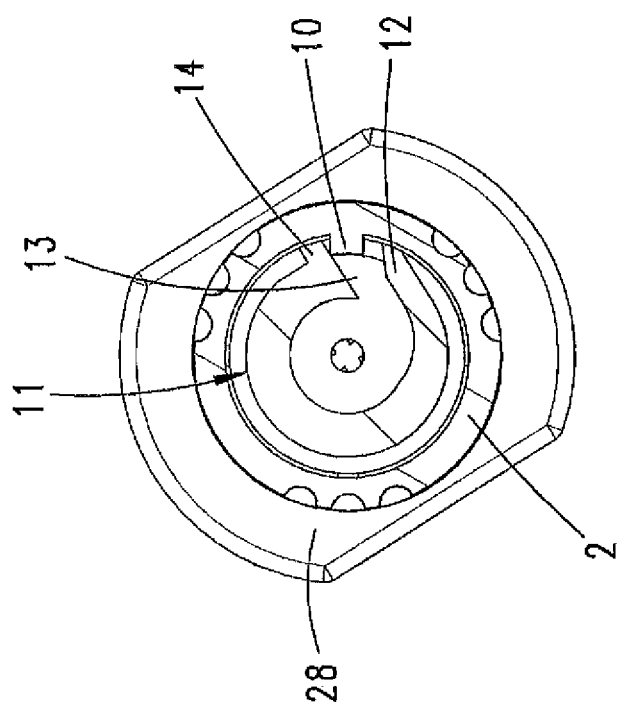

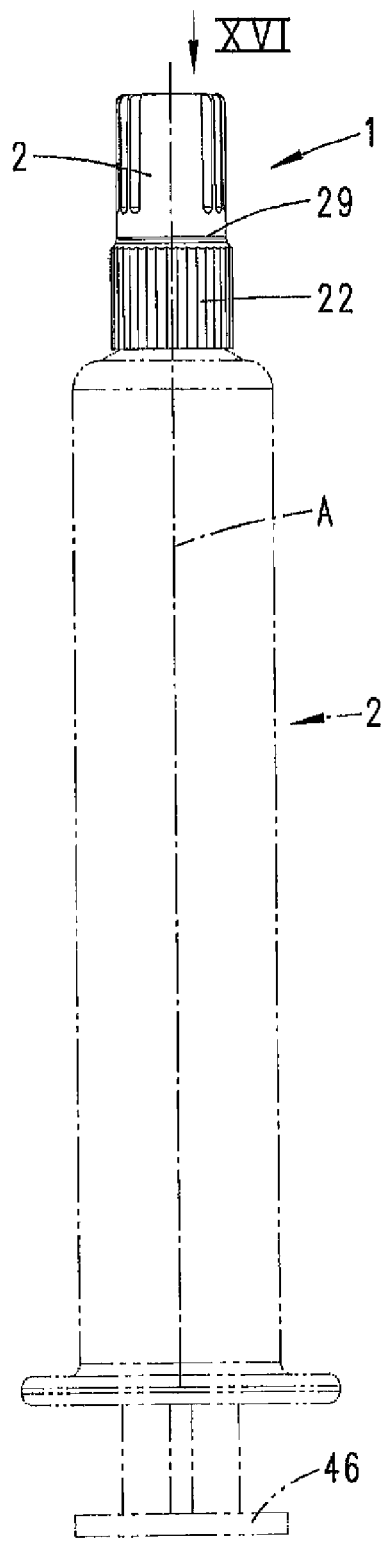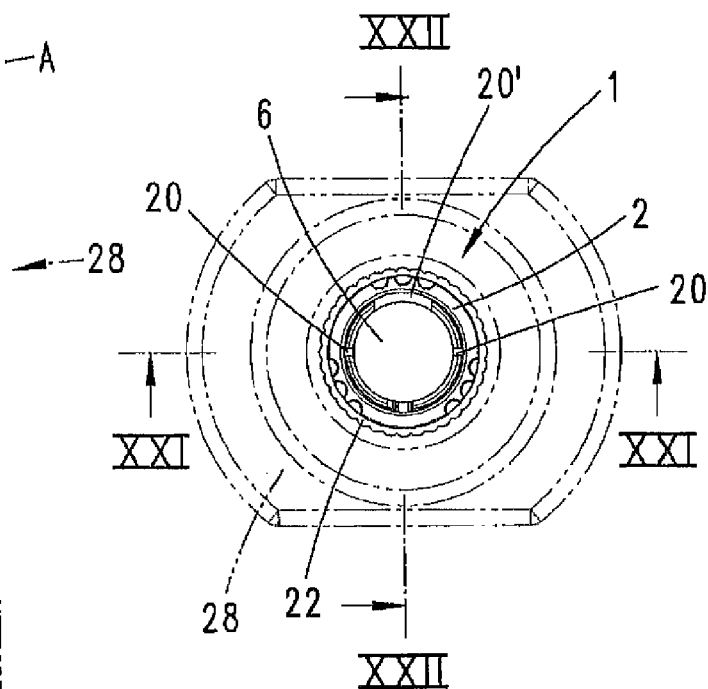

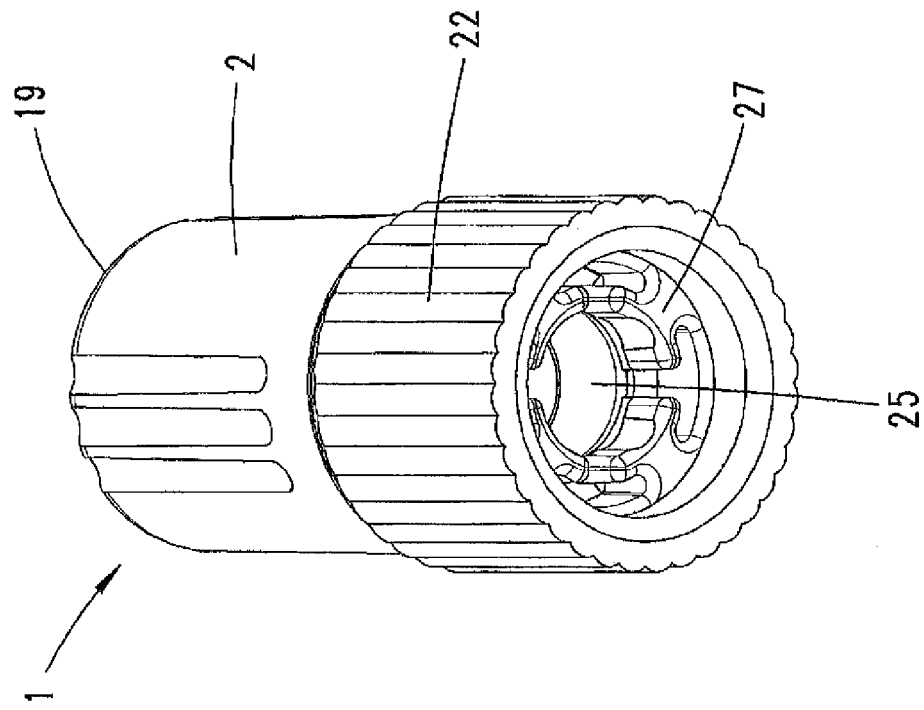
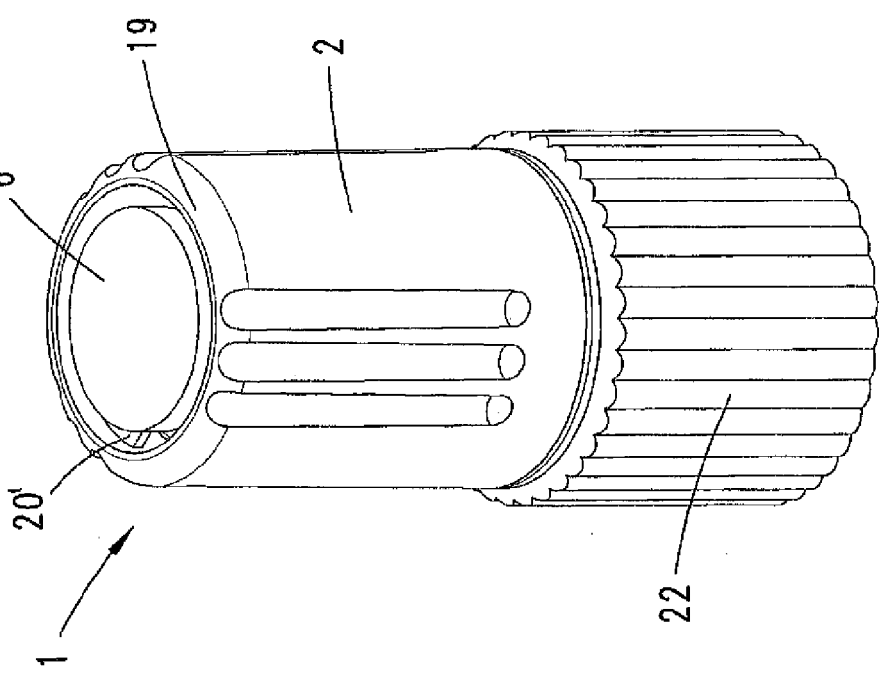

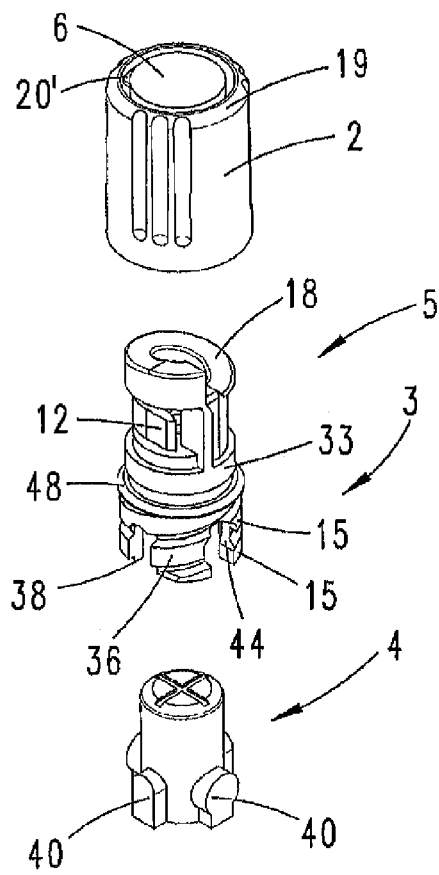
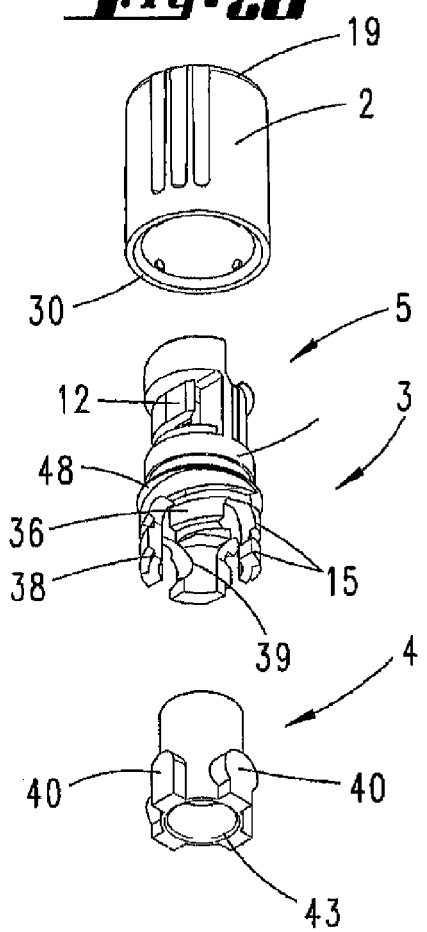
Fig. 19 Fig. 20
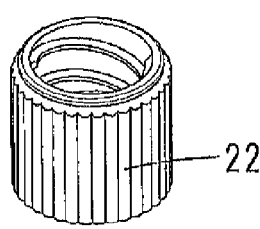
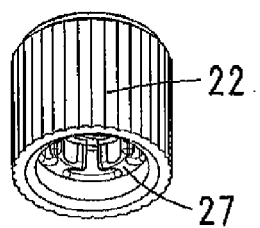
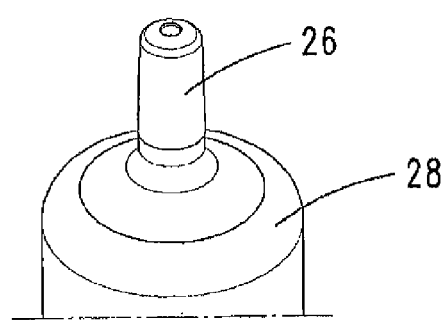
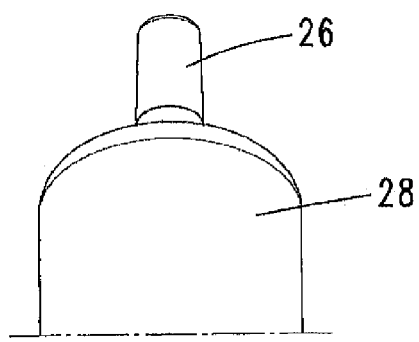

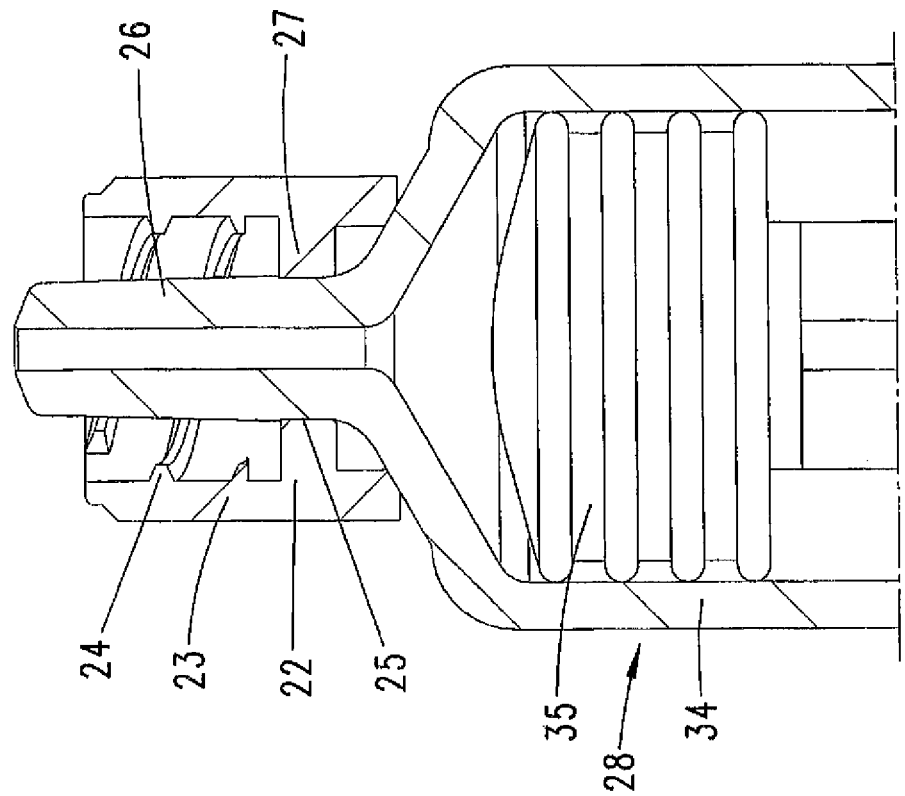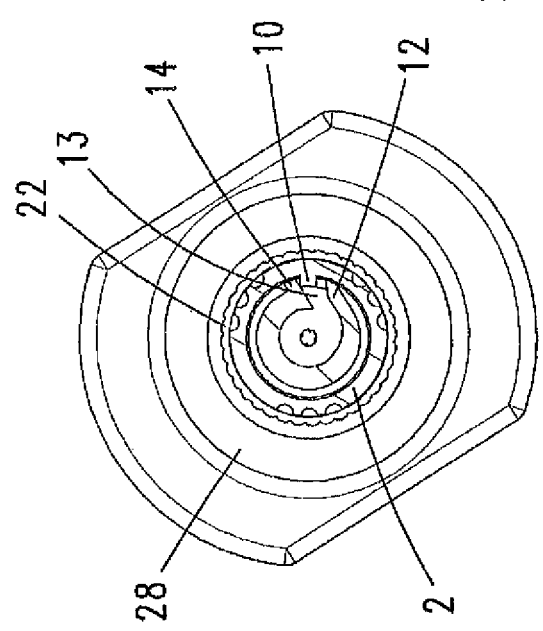

SYRINGE CAP

CROSS REFERENCE TO RELATED APPLICATIONS

This application is the National Stage of PCT/EP2011/071471 filed on Dec. 1, 2011, which claims priority under 35 U.S.C. §119 of German Application No. 10 2010 061 061.5 filed on Dec. 7, 2010, the disclosure of which is incorporated by reference. The international application under PCT article 21(2) was not published in English.

BACKGROUND OF THE INVENTION

1. Field of the Invention

The invention relates to a syringe cap for a medical syringe, comprising two cap parts that are moveable toward one another, a movement of the cap parts toward one another taking place when the syringe cap is removed for the first time from the syringe, and by virtue of this, a displacement of an indicator element takes place.

2. The Prior Art

Such syringe caps that are also designated as syringe end caps or tip caps are known in varied respects. For example, reference is to be made to an item of prior art according to U.S. Pat. No. 6,196,998 B1. In the case of the syringe cap known therefrom, two cap parts are provided—a first cap part that forms a distal end region of the syringe cap, and a second cap part that forms a proximal end region of the syringe cap. "Proximal" means here that after fitting the syringe cap onto the syringe, it is disposed facing the cylindrical part of the syringe body, which cylindrical part has a plunger part. These cap parts are connected to one another via predetermined breaking webs. In the course of a first unscrewing of the syringe cap from the syringe, the cap part forming the distal end region is separated from the further cap part by tearing it off. By this, a first use is detectable. The cap part associated with the distal end can be removed from the syringe while the other cap part remains on the syringe.

SUMMARY OF THE INVENTION

Proceeding from the illustrated prior art, the invention is concerned with the technical problem of providing a syringe cap for a medical syringe that provides an advantageous detectability of first use together with simple handling.

This technical problem is solved according to a first teaching of the invention for a syringe cap in which an indicator element is provided, and the indicator element can be removed from the syringe together with the cap parts. The indicator element is formed on the part that can be removed as a whole from the syringe. No part needs to remain on the syringe.

Further features of the invention are described and illustrated, including in the description of the figures and the drawing, often in their preferred association with the concept already explained above; however, they can also be of importance in association with only one or a plurality of individual features that are described here or illustrated in the drawings, or independently or in another overall concept. In particular, the features that the indicator element is located on the distal side of the syringe cap, that in the region of the thread formation of the syringe cap, in particular the inner cap, a brake formation is provided, that in first instance, the cap parts are twistable relative to one another and then can be transferred into a latching position resulting in a twist coupling, and/or that the inner cap consists of a sealing part with a screw part, have independent significance.

Preferably, in first instance, it is provided that the indicator element is located on the distal side of the syringe cap. It is also preferred that the indicator element is associated with the outer end of the syringe cap. This ensures straightaway goad visibility.

Furthermore, it is preferred that on a cap part, one or a plurality of thread turns are formed for interacting with a mount part having a mating thread. The mount part is preferably a mount collar surrounding a Luer connection on the syringe. It is also provided here that the one or in any case one of the thread turns formed on the cap part, or a groove formation between portions of the thread turn(s), has a brake formation. Due to the fact that a thread turn has a brake formation, unscrewing the syringe cap is counteracted by a certain resistance. This resistance can help prevent a syringe cap from being unscrewed unintentionally. However, as explained below, said resistance can also be utilized for moving the indicator element into the indicating position.

It is particularly preferred that in first instance, the cap parts are twistable relative to one another, and at the end of their relative twisting, can be transferred into a latching position that results in a twist coupling. The brake formation on the thread turn(s) is in particular of advantage with regard to this transferability into the latching position. By this, it can be arranged that when twisting off the syringe cap, first the transfer of the cap parts into the twist coupling takes place in a reliable manner, and only then, is unscrewing of the syringe cap from the syringe carried out during further screwing activity.

In further detail, it is preferred that the outer cap is a first movable cap part and that within the outer cap, an inner cap part is located that has the thread turn(s). Here, the outer cap part is provided to be movable relative to the inner cap part, in particular rotatable. Nevertheless, the thread turn formed on the inner cap part is preferably associated with an outer surface of the syringe cap. The thread turn is preferably formed on that region of the inner cap that extends below a lower peripheral edge of the outer cap.

In further detail, the inner cap part can consist of a sealing part and a screw part. The sealing part is provided for actually sealing the mouth of the syringe. It preferably consists of a rubber material or elastomer material. It can be press-molded and vulcanized or injection-molded. The screw part and the outer cap preferably are hard plastic parts produced using the injection molding method. The screw part preferably provides mainly the screw connection to the syringe body. The screw part preferably also provides the mount of the outer cap part on the inner cap part.

Furthermore, it is preferred that the sealing part forms a part of the outer surface of the screw part. For this, passage of part portions of the screw part through the sealing part, for example, one or a plurality of corresponding openings in the screw part, can be provided, so that the outer surface of the screw part is partially formed by the sealing part. Said passages are located in particular in the region of a thread turn or between two thread turns. Since the sealing part preferably consists of a rubber and/or elastomer material, it therefore can assume the function of the brake element on the inner cap part. It is preferably also provided that for this purpose, the sealing part is formed with a slightly greater extent, in particular in the radial direction. It is in particular provided that for forming the brake part, one or a plurality of axially extending positive locking formations are formed on the sealing part. These positive locking formations are fitted into corresponding positive locking recesses of the screw part. The positive locking recesses of the screw part can in particular be cut-outs that extend from the proximal end of the screw part and extend substantially axially.

It is further preferred that on one of the cap parts, preferably on the inner cap part, more preferably on the screw part, a run-on ramp is formed, by means of which, during the first twisting of the cap parts in the course of unscrewing the syringe cap from the syringe, the indicator element is moved into the indicating position. Also, the indicator element is preferably moved by this into the indicating position, with the tear-off webs being destroyed. The indicator element or a part acting on the indicator element can be moved by running onto the run-on ramp in the course of the twisting of the cap parts relative to one another.

With regard to the mount part, on the one hand, it is preferred that it is molded directly onto the syringe. This is in particular the case for syringe bodies that are completely produced using the injection molding method. This [mount] is usually a collar-shaped formation having an internal thread that surrounds the Luer connection.

However, alternatively, the syringe cap described herein can also be provided for syringes, in particular glass syringes, on which no mount collar with a corresponding thread is molded. For this it is then preferably provided that the syringe cap described herein is additionally provided with a mount part at its proximal end. More preferably, the mount part is provided with a central passage opening for connecting, preferably in the region of the Luer connection, to the neck of a syringe body. The connection can be a clamping connection and/or a positive connection. When unscrewing the syringe cap from the syringe, the mount part remains on the syringe. For securing on the syringe, the mount part can be fitted onto the syringe by means of pressure that results in a corresponding elastic widening and then in the desired clamping fit.

BRIEF DESCRIPTION OF THE DRAWINGS

The invention is further explained below with reference to the accompanying drawings which, however, illustrate only an exemplary embodiment. In the figures:

FIG. 1 shows a side view of a syringe with a syringe cap, said syringe being indicated only;

FIG. 2 shows a top view of the subject matter according to FIG. 1;

FIG. 3 shows a perspective view obliquely from above of the syringe cap;

FIG. 4 shows a perspective view obliquely from below of the syringe cap;

FIG. 5 shows an exploded view of the syringe cap and the associated end of the syringe in a view obliquely from above;

FIG. 6 shows an illustration according to FIG. 5 in a view obliquely from below;

FIG. 13 shows a cross-section through the subject matter according to FIG. 12, cut along the line XIII-XIII;

FIG. 14 shows a cross-section through the syringe body after removing the closing cap;

FIG. 15 shows a side view of a further indicated syringe body with a syringe cap of a second embodiment;

FIG. 16 shows a top view of the subject matter according to FIG. 15;

FIG. 17 shows the syringe body [sic; cap] of the second embodiment in a perspective view obliquely from above;

FIG. 18 shows the syringe body [sic; cap] of the second embodiment in a perspective view obliquely from below;

FIG. 19 shows an exploded view of the syringe body [sic; cap] of the second embodiment in a perspective view obliquely from above;

FIG. 20 shows an illustration according to FIG. 19 in a perspective view obliquely from below;

FIG. 27 shows a top view of the subject matter according to FIG. 26, and

FIG. 28 shows a cross-sectional view of the syringe after the syringe cap of the second embodiment has been unscrewed.

DETAILED DESCRIPTION OF THE PRESENTED EMBODIMENTS

Figure 7:
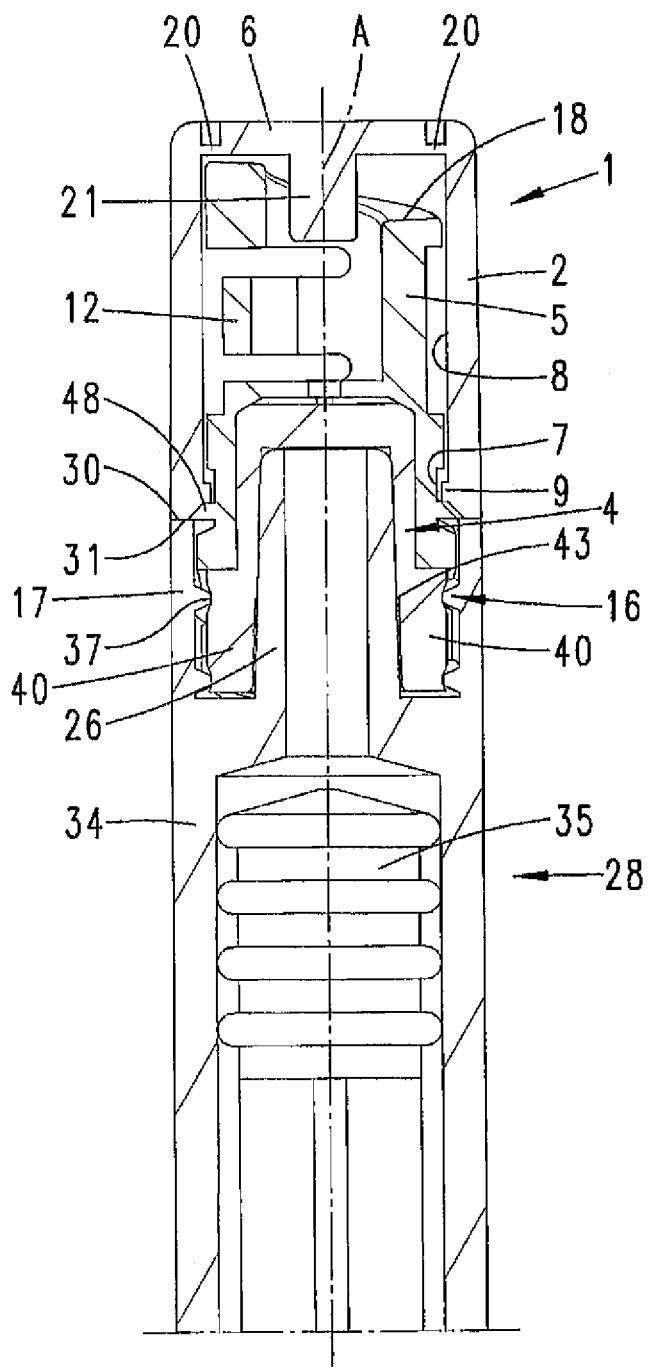
FIG. 7 shows a cross-section through a syringe cap fitted onto a syringe having a mount formation molded thereon, prior to the first unscrewing, and limited to the upper region of the syringe.

Illustrated and described in the first instance is a syringe cap 1 of a first embodiment which, as in particular shown with regard to the FIGS. 5 and 6, consists of an outer cap 2 and an inner cap 3, the inner cap 3 in the exemplary embodiment preferably being composed of a sealing part 4 and a screw part 5.

As shown in FIG. 1, the outer cap 2, which is the only visible part in the attached state, forms, with regard to the syringe 28, the distal end of the assembly of syringe cap 1 and syringe 28. By "distal", an end region is meant that faces away from a cylindrical part 34 of the syringe body, which cylindrical part accommodates a plunger part 35. In this particular end region of the syringe, this results in the appearance of a two-component design with a parting line 29 running perpendicular to a longitudinal axis A of the syringe 28 (and also of the syringe cap 1). The parting line 29 results from the lower edge 30 of the outer cap 2 and the upper edge 31 of the mount 17. As shown, in the longitudinal direction of the syringe 28, the outer cap 2 is formed in alignment with, the contour of the syringe 28.

The plunger part 35 can be longitudinally moved in a usual manner in the syringe 28 by means of a handle 46.

Figure 10:
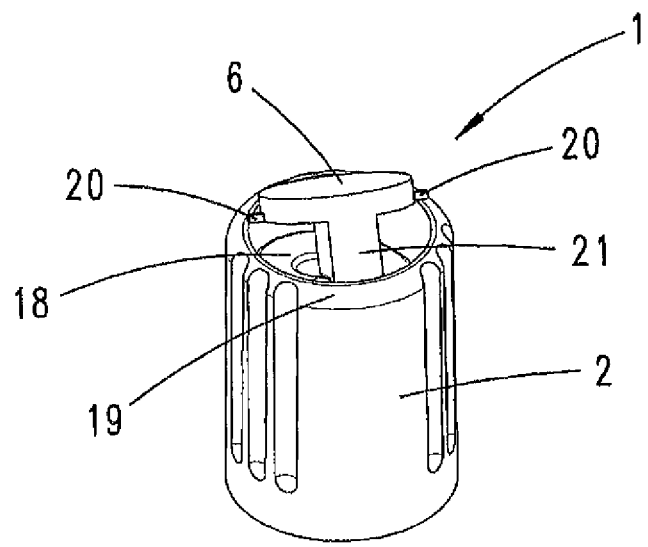
FIG. 10 shows a perspective view obliquely from above of the syringe cap after the first unscrewing from the syringe, and with the indicator element displaced into the indicating position.
Figure 11:
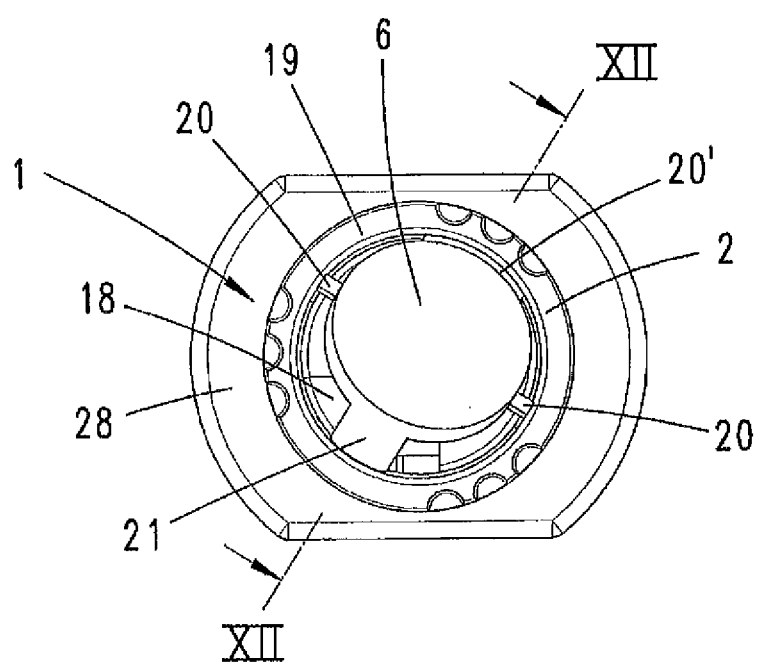
FIG. 11 shows a top view of the subject matter according to FIG. 10.

In the outer cap 2, an indicator element 6 is formed that can be displaced into an indicating position, as illustrated, for example, in the FIGS. 10 and 11 and, respectively, 24 and 25.

Prior to the first use, the indicator element is connected to the outer cap 2 by means of tear-off webs, in the exemplary embodiment two tear-off webs 20, that are disposed opposite one another. Furthermore, a film hinge 20' is provided. By this, the indicator element 6 remains connected to the outer cap 2 also in the indicating position. In the top view, the indicator element 6 has a round, preferably circular contour. More preferably, the outer cap 2 is configured as a thimble-like sleeve, the indicator element 6 forming the end face or a substantial part of the end face.

Figure 21:
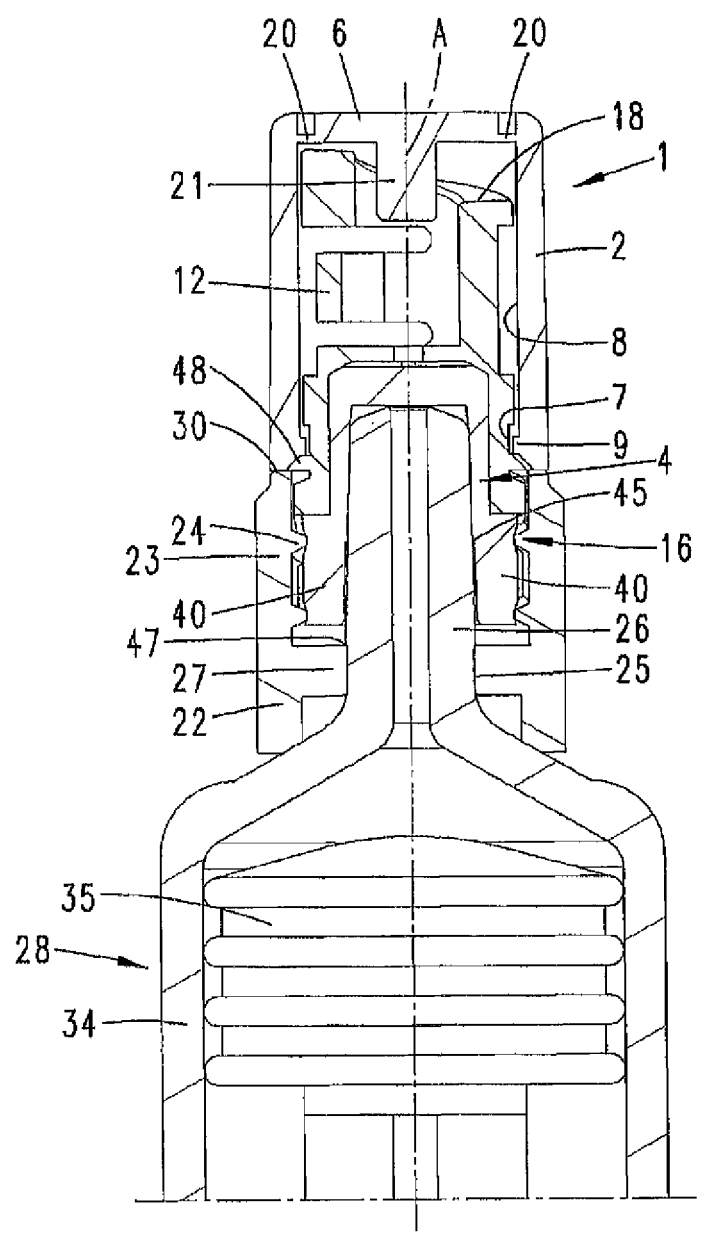
FIG. 21 shows a cross-sectional view of the syringe body [sic; cap] of the second embodiment fitted onto a syringe, prior to a first unscrewing of the syringe cap.
Figure 22:
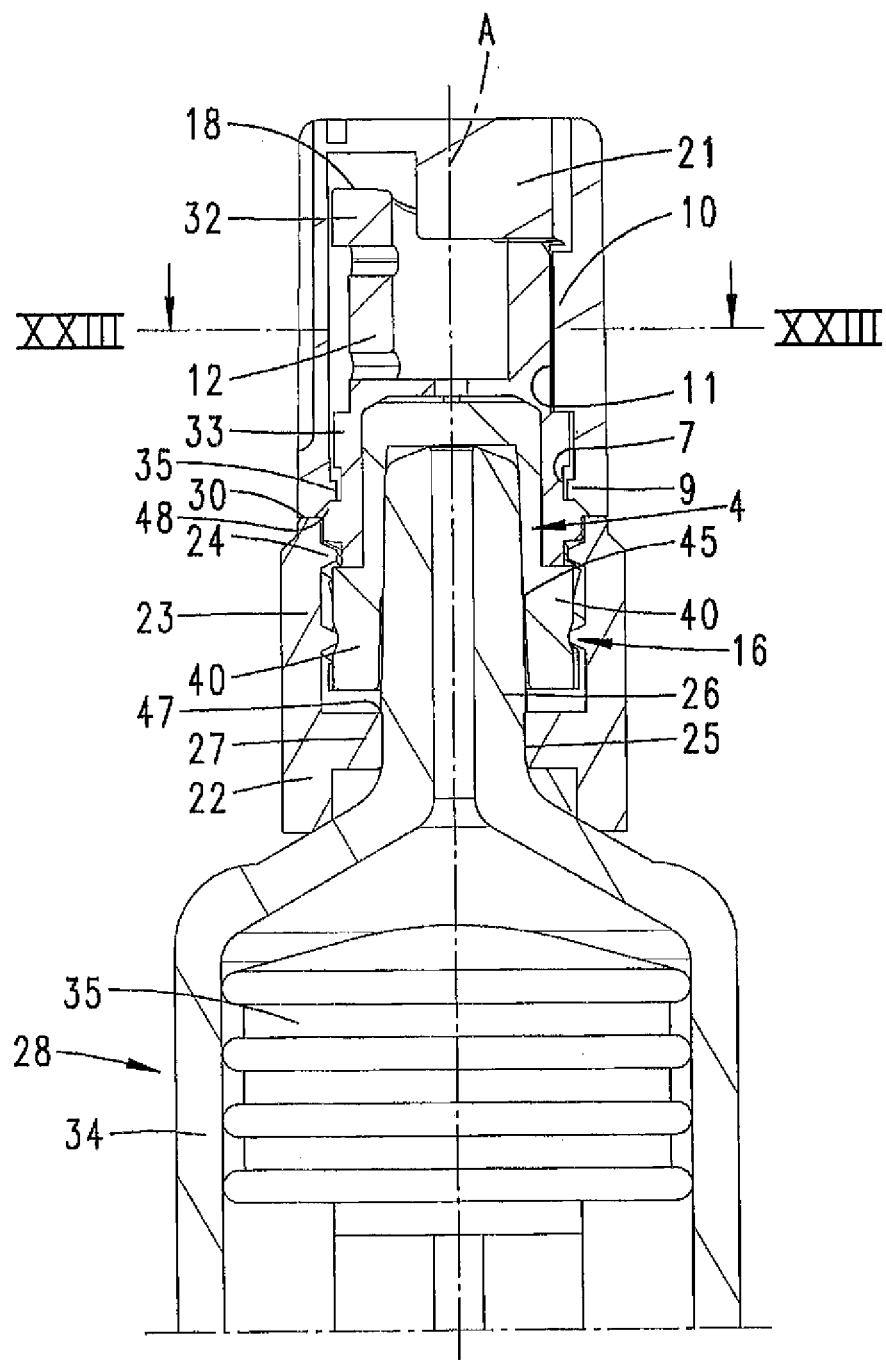
FIG. 22 shows a cross-section according to FIG. 21 in a cross-sectional plane offset by ninety degrees.

The outer cap 2 and the inner cap 3 form two cap parts that are movable, namely twistable, relative to one another. For this purpose, to be more specific, the outer cap part 2 as shown, for example, in the FIGS. 7 and 21, is accommodated in a positive locking recess 7 of the inner cap 3, preferably of the screw part 5. For this, the outer cap part has an engagement projection 9 that protrudes with respect to an inner surface 8 and engages in the recess V.

Preferably, and also in the exemplary embodiment, the outer cap 2 is twistable relative to the inner cap part 3, or specifically preferably relative to the screw part 5, about an axis of rotation that coincides with the longitudinal axis A of the syringe cap. Furthermore, the twistability is preferably provided in such a manner that in the course of the twisting of the outer cap part 2 relative to the inner cap 3, no telescopic movement occurs. Rather, for a given point of the outer cap part 2, this results only in a movement in a plane extending transverse to the longitudinal axis A of the syringe cap, said plane, more preferably, running perpendicular to the longitudinal axis A. It is also preferred that the twisting movement is possible only over an angular range of less than 360°.

Figure 9:
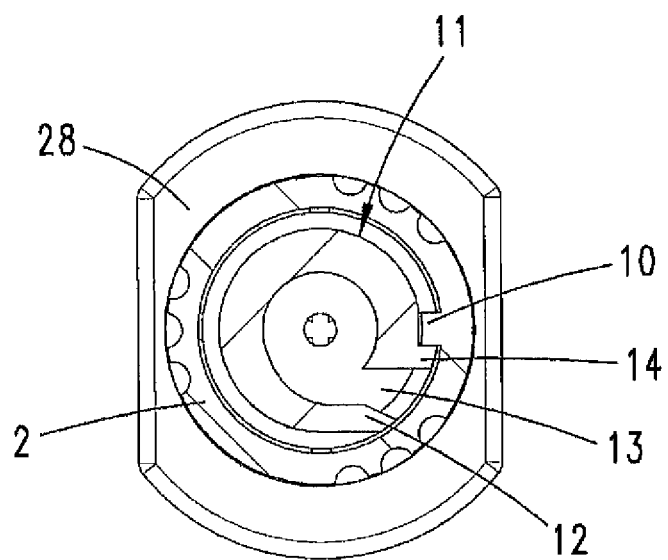
FIG. 9 shows a cross-section through FIG. 8, cut along the line IX-IX.
Figure 23:
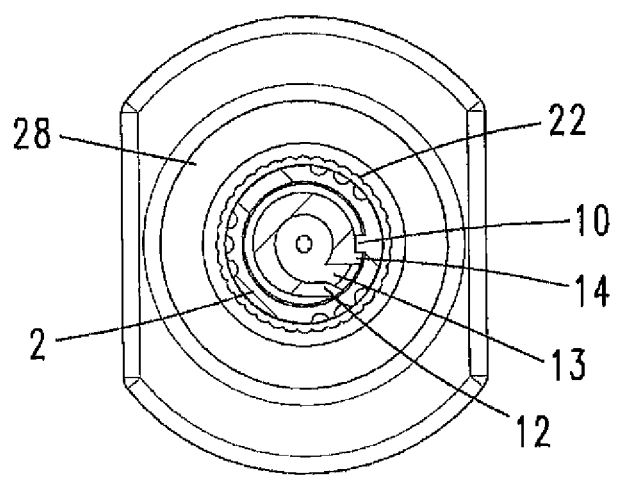
FIG. 23 shows a cross-section through the subject matter according to FIG. 22, cut along the line XXIII-XXIII.
Figure 24:
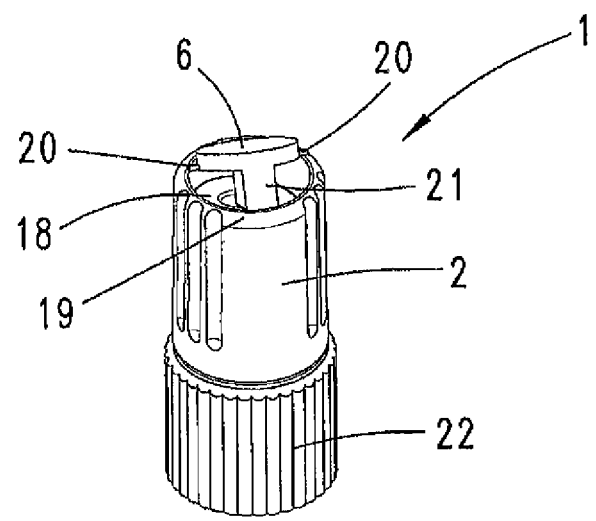
FIG. 24 shows an illustration according to FIG. 10 of the syringe cap of the second embodiment.
Figure 25:
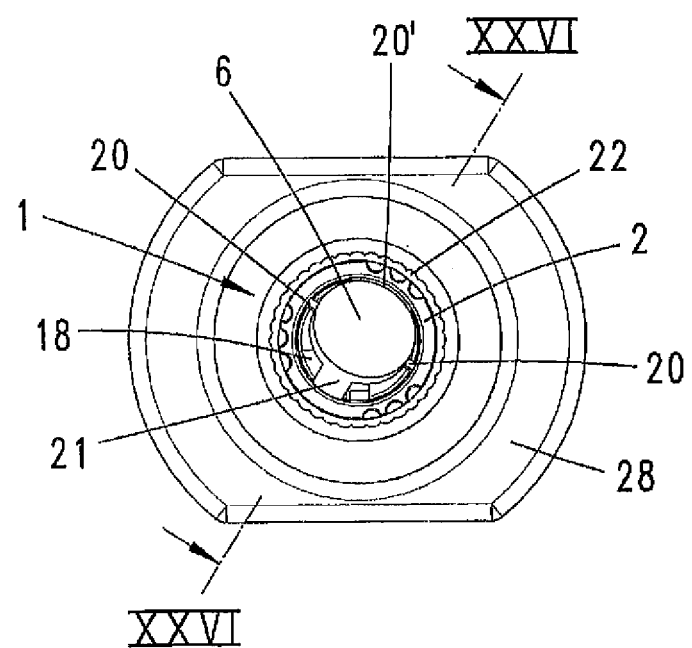
FIG. 25 shows a top view of the subject matter according to FIG. 24.

As shown, for example, in the FIGS. 9 and 23, the outer cap 2 further comprises a latching projection 10 that extends axially. The latching projection 10 interacts first by means of its end face with a step-like portion 11, of reduced diameter, of the inner cap 3 or preferably of the screw part 5. More preferably, due to a suitable axial extent, the latching projection 10 contributes to a stable guidance of the outer cap 2 on the inner cap 3, in any case during the twisting movement of the outer cap 2 relative to the inner cap 3. As likewise shown in FIG. 9, the wall of the step-like portion 11 of reduced diameter transitions in the peripheral direction into a latching formation 12 that protrudes radially outward and has a free end. When twisting the outer cap 2 relative to the inner cap 3 or, respectively, the screw part 5, the projection 10 runs over the latching formation 12 thereby elastically pushing the latter back radially inward until the latching projection 10—viewed in the peripheral direction—is aligned with a gap region 13 between the formation 12 and a stop wall 14, compare also FIGS. 13 and 17. Since subsequent to said overrunning, the formation 12 elastically springs back, the projection 10 is then caught in the gap region 13. Thus, a twist coupling between the cap parts, the outer cap 2 and the inner cap 3, is achieved. Further twisting of the syringe cap 2 results in the unscrewing of the syringe cap 2 from the syringe 28.

Also, this twist coupling is not reversible. When screwing the syringe cap onto the syringe 28 again, thus the same handling is given as for a syringe cap that, in this respect, is formed in one piece.

The inner cap 3, or preferably the screw part 5 of the inner cap 3, further comprises on the lower side of the setback region 11, more preferably below a step 33 and/or below the lower edge 30 of the outer cap 2, with regard to the interlocked state, one or a plurality of external thread turns 15. The region of the external thread turn(s) 15 is preferably formed such that it is set back inward with respect to the outer diameter of the outer cap 2 (in the lower region) by the dimension of a radial thickness of a mount 17. On the other hand, the largest diameter in the region of the thread turn(s) corresponds approximately to the outer diameter of the inner cap in the region of the step 33 or is even slightly larger.

The latching recess 7 is provided between the tapering portion 11 or, more preferably, the step 33, and the thread turn(s) 15. Also, the latching recess 7 is preferably formed as a setback. The engagement projection 9 engaging in this latching recess 7 is formed slightly offset upward with respect to the lower edge 30. Below the step 33 and above the thread turn(s) 15, more preferably on the screw part 5, a projection 48 is formed which preferably protrudes radially with respect to the thread turn(s) 15 and/or the step 33 and preferably is also chamfered on the upper side and extends circumferentially. In the assembled state, the inner side of the outer cap preferably rests, in the region of its lower edge 30, against this projection 48.

The tapering portion 11 that is preferably formed cylindrically is bounded toward the top by a radially protruding projection 32 that also extends circumferentially and horizontally with its lower edge. Overall, the axial mounting of the outer cap 2 on the inner cap 3 is achieved in this manner. The projection 32 forms on the upper side the run-on ramp 18 which is explained in more detail below.

With regard to a thread turn 15 or, respectively, an internal thread turn 37 (compare also FIG. 14) of the mount 17, said internal thread turn interacting with a groove formation 36 between two portions of the thread turn(s) 15 situated axially one above the other, a brake formation is provided. In the exemplary embodiment, and also preferably, the brake formation is provided by a section of the sealing part 4 that passes through passage openings 44 of the screw part 5. In this connection, reference is to be made in particular to FIGS. 3 and 4. By this, the inner cap part 3 interacts as a whole in the region of the thread turns 15 with the mount 17 of the syringe 28 in a braking manner such that during an attempted unscrewing of the syringe cap 1, first the described twisting between the outer cap 2 and the inner cap 3 takes place until the outer cap 2 is in the mentioned twist-lock position, whereby the twist coupling between the outer cap 2 and the inner cap part 3 is achieved. The elastic movability of the latching formation 12 formed in cross-section as an outwardly widening spiral portion is set in such a manner that as a result of the mentioned braking effect, the described overrunning of the latching portion 12 is first carried out before unscrewing of the syringe cap 1 from the syringe 28 takes place.

The passage openings 44 of the screw part 5 are formed in detail as axially extending openings that extend from the proximal end of a respective peripheral edge 38 of the screw part 5.

Preferably, passage openings 44 with an undercut 39 and passage openings 44 without an undercut 39 are formed in the screw part 5 and distributed over the periphery thereof. More preferably, there are two passage openings 44 with an undercut in the axial direction and two openings without an undercut in the axial direction. The openings without an undercut are configured substantially in an arch-shaped manner while the openings with an undercut are substantially configured in a mushroom-shaped manner in plan view.

Figure 8:
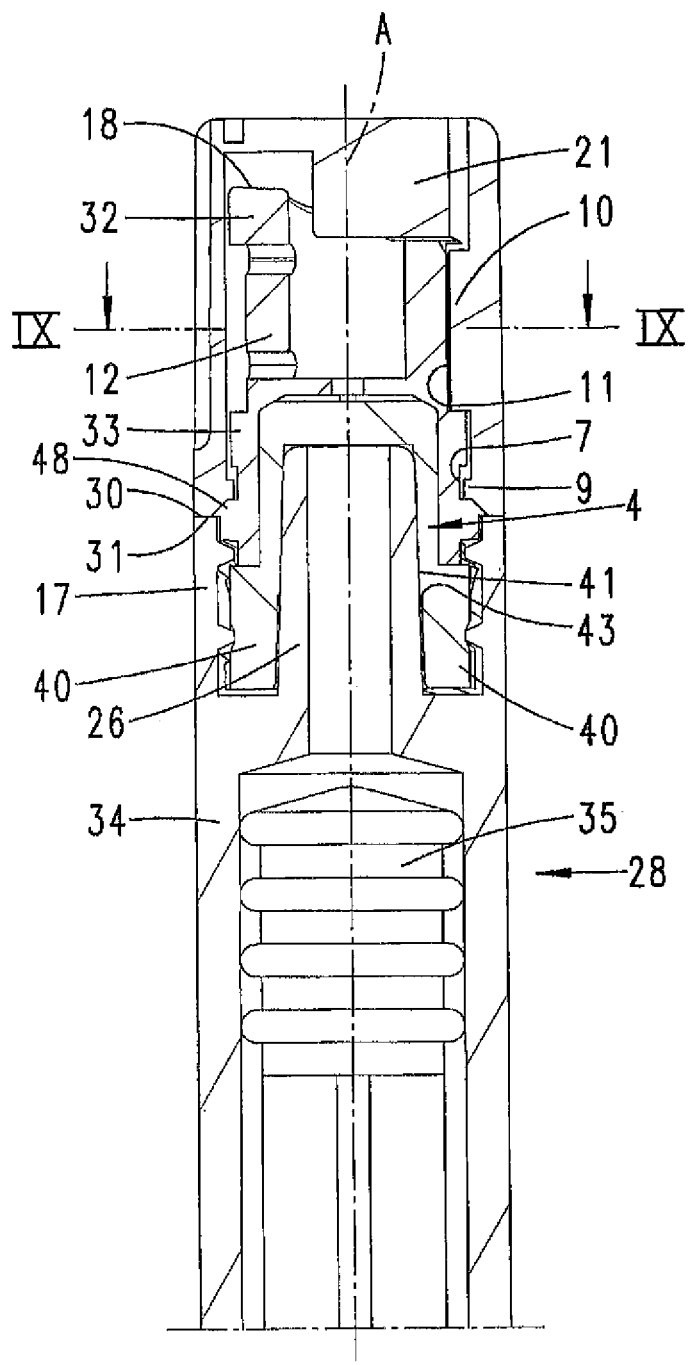
FIG. 8 shows an illustration according to FIG. 7, with a sectional plane that is offset by ninety degrees.

The sealing part 4 has correspondingly formed, radially projecting formations 40, compare in particular FIGS. 5, 6 and 19, 20, that likewise are formed corresponding to the arch-shaped plan view and the mushroom-shaped plan view of the passage openings 37 [sic; 37, 44], respectively. These formations too extend from the proximal end of the sealing part 4. These formations 40 are in particular the brake formations. For this purpose, it is preferably provided that they protrude into the groove formation 36. However, more preferably, they do not protrude radially beyond an axial outer surface of a thread turn 15. The deformations that arise in the screwed state due to the elastic configuration of the formations 40 are shown, for example, in the FIGS. 7 and 8 as well as 21 and 22.

Figure 12:
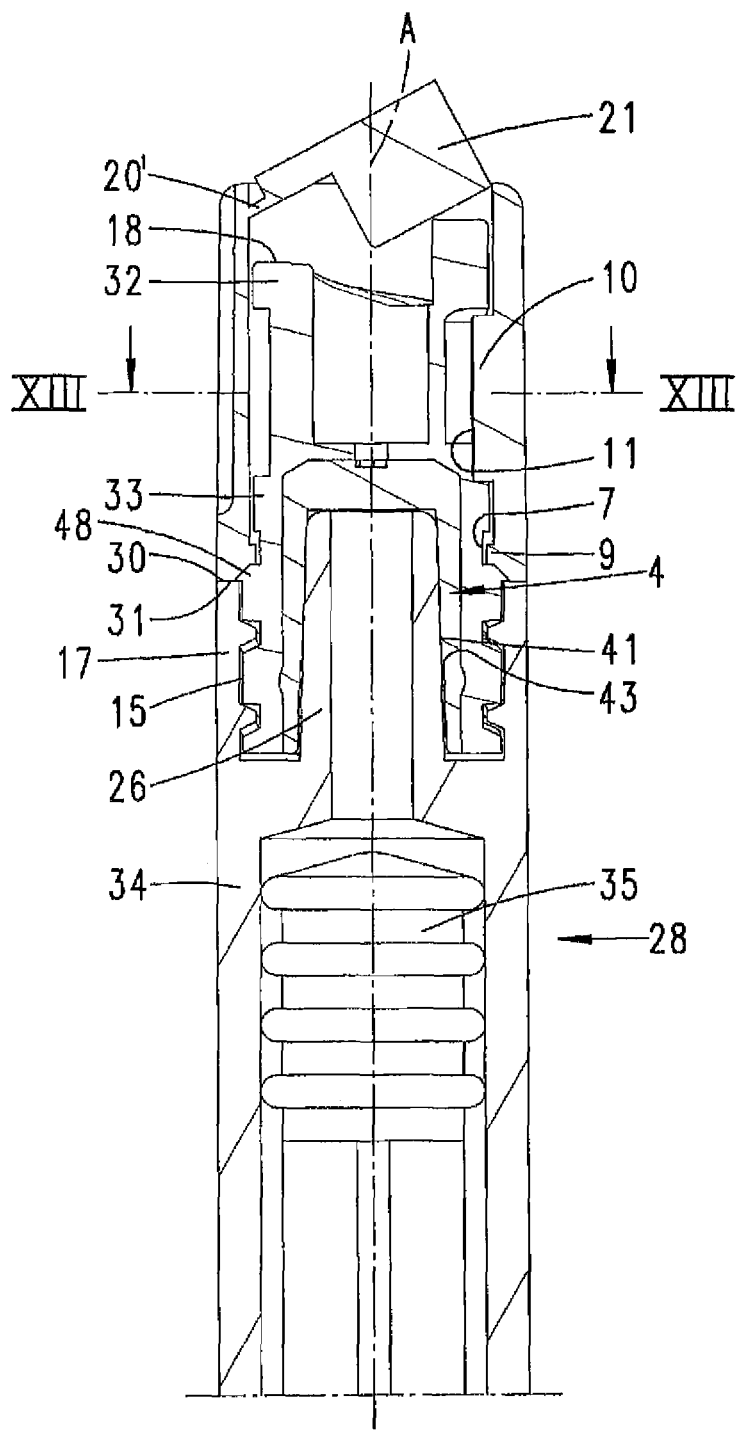
FIG. 12 shows a cross-section through the subject matter according to FIG. 11, cut along the line XII-XII.
Figure 26:
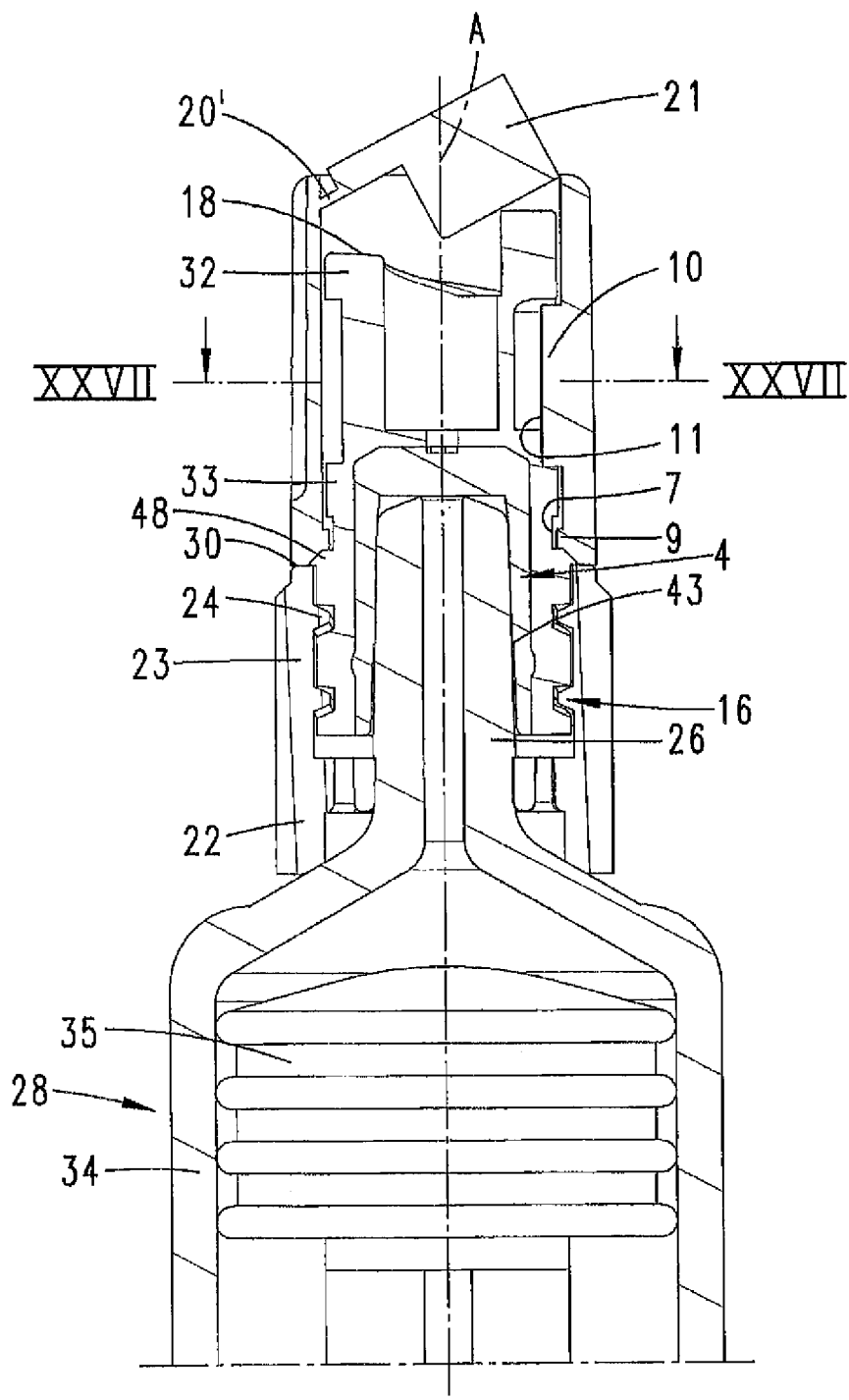
FIG. 26 shows an illustration of the syringe cap of the second embodiment after a first actuation, but prior to unscrewing from the syringe cap [sic; syringe body]

Apart from that, the sealing part 4 is configured substantially in a hat-shaped manner. Also, it preferably has a rotationally symmetric cross-section, except for the mentioned formations 40. Furthermore, a run-on ramp 18 (compare, for example, FIGS. 5 and 8) that extends circularly in plan view but rises in a spiral-like manner is formed on the screw part 5. When twisting the outer cap 2 relative to the inner cap 3, the indicator element 6 interacts with this run-on ramp 18. The interaction is preferably such that in the course of the twisting, the indicator element 6 is raised relative to an end edge 19 of the outer cap 2. For this, the indicator element 6 preferably has a run-on cam 21 on the lower side. By this, in the course of the twisting of the outer cap 2, which for all practical purposes does not move axially here, the indicator element is raised relative to the outer cap 2. One or a plurality of the tear-off webs 20, in the exemplary embodiment two tear-off webs 20, are severed when raising the indicator element 6 into the indicating position according to FIG. 10. As shown, the indicating position is given in that the indicator element 6 is displaced from a position having an extent that is approximately at right angles to the longitudinal axis A into a position that, in the vertical cross-section, is at an acute angle to the longitudinal axis A with regard to its main direction of extent. The remaining film hinge 20' (compare also FIGS. 2 and 12 or, respectively, 16 and 26) effects a quasi twist mounting of the indicator element 6. In the exemplary embodiment, the indicator element 6, with the exception of the run-on cam 21, is formed substantially plate-shaped, namely, as preferably also specified, as a plate part having a circular contour. The run-on cam 21 is preferably formed as a radially extending rib. As a further detail, this run-on cam 21 interacts with the run-on ramp 18. The raised or twisted state of the indicator element 6 cannot be set back again into the mentioned extent at right angles since the run-on cam 21, even in the twisted end state (twist coupling) of outer cap 2 and inner cap 3, is aligned with the run-on ramp 18, namely preferably aligned with an uppermost region of the run-on ramp 18. See also FIGS. 12 and 26 in this connection.

On the inner side, the sealing part 4 has a recess 41 that is adapted to the Luer projection 42 of the syringe 28. This recess 41 is completely closed, except for the opening 43 that is formed in the attached state in the proximal end of the sealing part 4. Offset toward the distal end of the syringe cap 1, the recess 41 is preferably provided with a circumferential shoulder 45. The recess 41, which preferably is also formed conically so as to be adapted to the Luer formation of the syringe, continues above the shoulder 45. This step-like tapering can contribute again to improve the sealing.

With regard to the second embodiment as illustrated in the FIGS. 15 to 28, similar parts are designated by the same reference numbers. The description in this regard of the first embodiment applies also to the second embodiment.

The second embodiment relates to the configuration of a syringe cap 1 for a syringe that is not formed with a mount formation 15 having an internal thread. Usually, this is a glass syringe.

In order to nevertheless make mounting of the syringe cap 1 on the syringe 28 possible, the syringe cap 1 of the second embodiment is provided with a mount part 22. The syringe cap 1, which can be screw-connected to the mount part 22 in the as-delivered condition prior to being fitted the first time onto the syringe 28, can be unscrewed from the mount part 22 after the combination of syringe cap 1 and mount part 22 is fitted. For this, the mount part 22 remains on the syringe 28; compare also FIG. 28.

As is apparent from FIG. 15, on the lower side, the mount part 22 is seated directly on the transition region of the syringe neck 26 into the cylindrical part 34 of the syringe 28. Preferably, the outer cap 2 is formed with a slightly smaller outer diameter than the mount part 22.

The mount part 22 forms a mount collar 23 with an internal thread 24. The internal thread 24 preferably corresponds to the internal thread of the mount part 17, as it is described in connection with the first embodiment.

The mount part 22 is provided with a central through-opening 25 by means of which it can be pushed over the neck 26 of the syringe, which neck forms the mouth. For this, a waisted portion of reduced diameter is formed on the neck 26, into which portion of reduced diameter, mount webs 27 of the mount are moved. As in particular shown in FIG. 18, in a horizontal projection, a mount web 27 is formed approximately T-shaped, the ends of the T-crossbar being formed projecting inwardly. On the lower side, thus in their region that, in the direction of attachment, first comes into contact with the syringe neck 26, the mount webs are formed rounded. In this way, they can resiliently deflect radially outward under elastic deformation—with regard to the cantilever regions of the T-bar—and thus can be moved fully into the mentioned undercut. In contrast, the edge on the upper side, as is apparent from FIG. 21, is provided with a comparatively sharp corner formation so that a desired latching is created behind a circumferential shoulder 47 formed on the syringe neck 26.

The arrangement of the mount part 22 with the outer cap part 2 and the inner cap 3 located therein, according to the FIGS. 17 and 18, can be used for a direct plug connection with a syringe as described, in particular a glass syringe.

All features disclosed are (in themselves) pertinent to the invention. The disclosure content of the associated/accompanying priority documents (copy of the prior application) is also hereby included in full in the disclosure of the application, including for the purpose of incorporating features of these documents in claims of the present application. The subsidiary claims in their optional subordinated formulation characterize independent inventive refinement of the prior art, in particular to undertake divisional applications based on these claims.

| | Reference list |
|---|---|
| 1 | Syringe cap |
| 2 | Outer cap |
| 3 | Inner cap |
| 4 | Sealing part |
| 5 | Screw part |
| 6 | Indicator element |
| 7 | Latching recess |
| 8 | Inner surface |
| 9 | Engagement projection |
| 10 | Latching projection |
| 11 | Portion of reduced diameter |
| 12 | Formation |
| 13 | Gap region |
| 14 | Stop wall |
| 15 | Thread turn |
| 16 | Internal thread |
| 17 | Mount |
| 18 | Run-on ramp |
| 19 | End edge |

| Reference list | |
|---|---|
| 20 | Tear-off webs |
| 20' | Film hinge |
| 21 | Run-on cam |
| 22 | Mount part |
| 23 | Mount collar |
| 24 | Internal thread |
| 25 | Through-opening |
| 26 | Syringe neck |
| 27 | Mount webs |
| 28 | Syringe |
| 29 | Parting line |
| 30 | Lower edge |
| 31 | Upper edge |
| 32 | Projection |
| 33 | Step |
| 34 | Cylindrical part (of 28) |
| 35 | Plunger part |
| 36 | Groove formation |
| 37 | Internal thread turn |
| 38 | Peripheral edge |
| 39 | Undercut |
| 40 | Formation |
| 41 | Recess |
| 42 | Luer projection |
| 43 | Opening |
| 44 | Passage openings |
| 45 | Shoulder |
| 46 | Handle |
| 47 | Shoulder |
| 48 | Projection |
| A | Longitudinal axis |

The invention claimed is:

1. A syringe cap for a medical syringe, comprising two cap parts that are moveable toward one another, a movement of the cap parts toward one another taking place when the syringe cap is removed for the first time from the syringe, and by virtue of this, a displacement of an indicator element into an indicating position takes place, and the indicator element can be removed from the syringe together with the cap parts of the syringe cap; and
   both cap parts are removable at once from the syringe together with the indicator element.

2. The syringe cap according to claim 1, wherein the syringe cap consists of an outer cap and an inner cap.

3. The syringe cap according to claim 1, wherein the cap parts are in first instance twistable relative to one another and at the end of their being twisted relative to one another, they can be transferred into a latching position that results in a twist coupling.

4. The syringe cap according to claim 3, wherein the twist coupling is not reversible.

5. The syringe cap according to claim 2, wherein in the course of the twisting of the outer cap part relative to the inner cap part, no telescopic movement results.

6. A syringe cap for a medical syringe, comprising two cap parts that are moveable toward one another, a movement of the cap parts toward one another taking place when the syringe cap is removed for the first time from the syringe, and by virtue of this, a displacement of an indicator element into an indicating position takes place, and the indicator element can be removed from the syringe together with the cap parts of the syringe cap; and
   wherein the syringe cap consists of an outer cap and an inner cap; and
   wherein the outer cap is configured as a thimble-like sleeve, the indicator element forming the end face or a substantial part of the end face.

7. The syringe cap according to claim 1, wherein the indicator element is located on the distal side of the syringe cap.

8. The syringe cap according to claim 2, wherein on the inner cap one or a plurality of thread turns are formed for interacting with a mount part on the syringe, and wherein a thread turn, or a groove formation between portions of the thread turn(s), has a brake formation.

9. The syringe cap according to claim 2, wherein the inner cap consists of a sealing part and a screw part.

10. A syringe cap for a medical syringe, comprising two cap parts that are moveable toward one another, a movement of the cap parts toward one another taking place when the syringe cap is removed for the first time from the syringe, and by virtue of this, a displacement of an indicator element into an indicating position takes place, and the indicator element can be removed from the syringe together with the cap parts of the syringe cap; and
   wherein the syringe cap consists of an outer cap and an inner cap; and
   wherein the inner cap consists of a sealing part and a screw part; and
   wherein the sealing part is formed from a rubber or elastomer material.

11. The syringe cap according to claim 9, wherein the sealing part forms a part of an outer surface of the screw part, for which purpose the sealing part preferably has formations that extend axially.

12. The syringe cap according to claim 11, wherein the formations are radially projecting.

13. The syringe cap according to claim 11, wherein the formations are seated in corresponding passage openings of the screw part.

14. The syringe cap according to claim 8, wherein the mount part is directly molded onto the syringe.

15. The syringe cap according to claim 8, wherein the mount part is formed separately from the cap parts.

16. The syringe cap according to claim 8, wherein the mount part has a central through-opening for connecting to the neck of a syringe body, preferably of a glass syringe.

17. The syringe cap according to claim 16, wherein the connection is a clamping connection and/or a positive connection.

18. The syringe cap according to claim 8, wherein on the mount part, a plurality of mount webs are provided, which in a horizontal projection are formed T-shaped.

* * * * *